(12) United States Patent
Craciun

(10) Patent No.: US 8,124,701 B2
(45) Date of Patent: Feb. 28, 2012

(54) FUNCTIONALIZED (METH)ACRYLIC MONOMERS AND POLYMERS FOR ACETYLENIC ALCOHOLS

(75) Inventor: Liliana Craciun, Carmel, NY (US)

(73) Assignee: BASF SE, Ludwigshafen (DE)

( * ) Notice: Subject to any disclaimer, the term of this patent is extended or adjusted under 35 U.S.C. 154(b) by 424 days.

(21) Appl. No.: 12/317,022

(22) Filed: Dec. 18, 2008

(65) Prior Publication Data

US 2009/0171008 A1 Jul. 2, 2009

Related U.S. Application Data

(60) Provisional application No. 61/009,393, filed on Dec. 28, 2007.

(51) Int. Cl.
*C08F 126/06* (2006.10)
(52) U.S. Cl. ......... 526/258; 526/261; 526/262; 526/263
(58) Field of Classification Search .................. 526/258, 526/261, 262, 263
See application file for complete search history.

(56) References Cited

U.S. PATENT DOCUMENTS

| | | | |
|---|---|---|---|
| 7,208,243 B2 | 4/2007 | Li et al. ............................. | 429/33 |
| 2006/0154129 A1 | 7/2006 | Li et al. | |
| 2007/0066762 A1 | 3/2007 | Acosta et al. ............. | 525/330.3 |
| 2007/0155953 A1 | 7/2007 | Li et al. | |
| 2008/0266519 A1 | 10/2008 | Schlueter ...................... | 351/160 |

OTHER PUBLICATIONS

Click Chemistry, Review by Kolb H.C., et al., Angew.Chem. Int. Ed. 2001, 40, 2004-2021.
Huisgen R. , Proceedings of the Chemical Society, 1961, 357369.
Huisgen RI, Angew. Chem. 1968, 80, 329337.
Vogt A. P. et al., Macromolecules 2006, 39, 5286-5292.
Liu Q, et al., Journal of Polymer Science; Part A: Polymer Chemistry, vol. 44, 61036113 (2006).
Opsteen j.A., et al., Chem. Commun., 2005, 5759.
Macromolecules 2005, 38, 75407545, Sumerlin B.S., et al.
Journal of Polymer Science: Part A: Polymer Chemistry 2004, 42, 4392-4403, Diaz D.D., et al.
Riva R. ,et al, Arkivoc 2007, 10, 292-306.
International Search Report dated Jun. 8, 2009.

*Primary Examiner* — Edward Cain
(74) *Attorney, Agent, or Firm* — Shiela A. Loggins

(57) ABSTRACT

The invention is directed to novel 1,2,3-triazoles containing (meth)acrylate monomers of formulae (I) and (II)

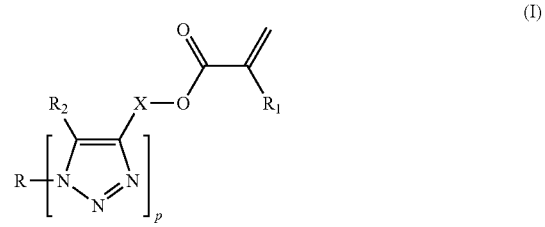

(I)

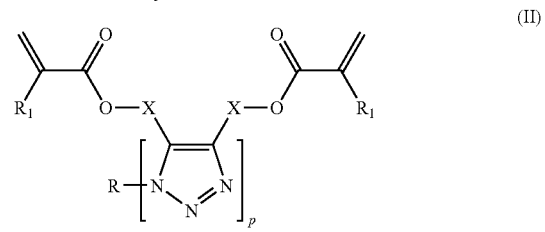

(II)

Wherein R, $R_1$, $R_2$, X and p defined herein and the process of making said monomers and (co)polymers formed from.

11 Claims, No Drawings

US 8,124,701 B2

FUNCTIONALIZED (METH)ACRYLIC MONOMERS AND POLYMERS FOR ACETYLENIC ALCOHOLS

This application claims the benefit of Provisional Application No. 61/009,393, filed Dec. 28, 2007 herein incorporated entirely by reference.

FIELD OF THE INVENTION

The invention is directed to novel 1,2,3-triazoles containing (meth)acrylate monomers. The invention also embodies the process of making said monomers and (co)polymers formed there from.

BACKGROUND

The Huisgen 1,3-dipolar cycloaddition of alkynes and azides to form 1,4-disubstituted-1,2,3-triazoles has been established as one of the most reliable means for carbon-heteroatom bond forming "click chemistries". The term "click" reaction generally refers to a reaction that is high yielding, stereospecific for a single product, and easy to perform with regard to starting materials, solvent, or product isolation. "Click" reactions are invariant to the presence of air or moisture, and tolerant to a wide range of functional groups. See for example, a recent "click chemistry" review by Kolb H. C. et al, *Angew. Chem. Int. Ed.* 2001, 40, 2004-2021. Also, see Huisgen R., *Proc. Chem. Soc.* 1961, 357-369, and Huisgen R., *Angew. Chem.* 1968, 80, 329-337.

The present invention discloses novel triazole-based monomers synthesized via a "click chemistry" approach. In particular, the present invention describes a group of novel (meth)acrylates containing 1,2,3-triazole moieties. The new (meth)acrylate monomers may be formed via the Cu(I)-catalyzed Huisgen 1,3-dipolar cycloaddition of azides with acetylenic (meth)acrylic esters such as propargyl acrylate. These "click" reactions give access to a new monomer family of triazole-based (meth)acrylates.

The literature discloses numerous references where macromers or dendrimers, prepared via atom transfer radical polymerization (ATRP) or other controlled polymerization methods, are derivatized to contain azido end-groups. Reaction of the azido-terminated macromers with alkyne-containing (meth)acrylates results in the formation of derivatized end-capped macromers containing (meth)acrylate functionalized 1,2,3-triazoles. For example, see Vogt A. P. et al, *Macromolecules* 2006, 39, 5286-5292, and Liu Q. et al, *J. of Polymer Science: Part A: Polymer Chemistry*, vol. 44, 6103-6113. Furthermore, Opsteen J. A. et al, *Chem. Commun.*, 2005, 57-59, discusses the modular synthesis of block co-polymers via 1,3-cycloaddition of terminal azides with alkyne-functionalized polymers. Also, in *Macromolecules* 2005, 38, 7540-7545, Sumerlin B. S. et al reports the use of the highly efficient "click" reaction to prepare poly(triazoles) by coupling poly(3-azidopropyl methacrylate) with alkynes.

U.S. Pat. No. 7,208,243 discloses azide-alkyne cycloaddition reactions to prepare cross-linked polymers. The cross-linked polymers may be formed from a first alkyne functionalized polymer and a second azide functionalized polymer, a single polymer species which may include both azide and alkyne groups and cross-links with itself, or a polymer with azide groups and a non-polymer compound including one or more alkyne groups. Similarly in *J. of Polymer Science: Part A: Polymer Chemistry* 2004, 42, 4392-4403, Diaz D. D. et al employs the coupling of polyvalent azides and alkynes to make cross-linked polymeric networks of 1,2,3-triazoles, with good adhesion to metal surfaces.

U.S. Application Publication No. 2007/0066762 discloses triazole-containing perfluorinated acrylic monomers. The monomers are co-polymerized for imparting water repellence and stain resistance to substrates.

Furthermore, Riva R. et al, ARKIVOC 2007, 10, 292-306, discloses acrylates formed by 1,3-cycloaddition of various alkynes with 5-azidooxepan-2-one.

There exists however, a continuing need for novel monomers such as those presently described.

SUMMARY OF THE INVENTION

Monomers represented by formulae (I) and (II) are embodied in the invention:

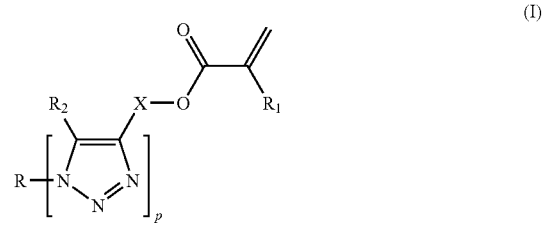

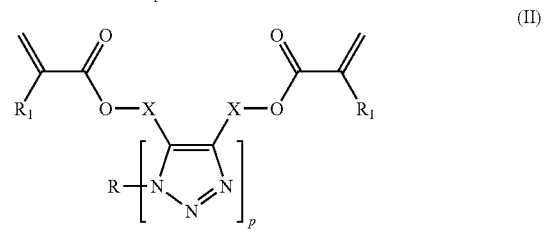

wherein
$R_1$ is hydrogen or $C_{1-3}$ alkyl,
$R_2$ is hydrogen, methyl, linear or branched $C_{2-30}$ alkyl,
  where said $C_{2-30}$ alkyl is optionally interrupted by O, S or Si,
  and is optionally further substituted by phenyl, $OR_3$, $COOR_4$ or $NR_5R_6$;
X is methylene or linear or branched $C_{2-30}$ alkylene, optionally substituted by one or more phenyl,
  wherein $C_{2-30}$ alkylene is optionally interrupted by O or S;
p is 1, 2, 3 or 4;
when p is 1,
R is hydrogen, methyl, linear or branched $C_{2-30}$ alkyl, cycloalkyl, $C_{2-30}$ alkenyl, aryl, aralkyl, heterocycloalkyl or heterocycloaryl,
  wherein the alkyl or alkenyl is optionally interrupted by O or S, and
  is optionally further substituted by one or more halogen, OH, $C_{1-4}$ haloalkyl, $C_{1-16}$ alkyl, phenyl, $OR_3$, $COOR_4$ or $NR_5R_6$;
when p is 2, 3 or 4,
R is a di-, tri- or tetra-valent linking group,
  said linking group is a polymer, methylene, linear or branched $C_{2-20}$ alkylene, cycloalkylene, linear or branched $C_{2-30}$ alkenylene, arylene, aralkylene, heterocycloalkylene or heterocycloarylene,
  the $C_{2-30}$ alkylene or $C_{2-30}$ alkenylene is optionally interrupted by O or S, and the aryl or the arylene group, the aryl of the aralkyl, the cycloalkylene, the heterocycloalkylene or heterocycloarylene is optionally further substituted by one or more halogen, OH, $C_{1-4}$ haloalkyl, $C_{1-16}$ alkyl, substituted or unsubstituted phenyl, $OR_3$, $COOR_4$ or $NR_5R_6$;

$R_3$ is linear or branched $C_{1-10}$ alkyl or phenyl;

$R_4$ is linear or branched $C_{1-10}$ alkyl or phenyl;

and $R_5$ and $R_6$ are independently hydrogen, linear or branched $C_{1-10}$ alkyl, or $R_5$ and $R_6$ together form a ring.

Furthermore, the polymers or co-polymers formed from the monomers described by formulae (I) and (II) are also embodied in the present invention.

Monomers of formulae (I) and (II) may be formed from either method (a) or method (b) described below.

Method (a) comprises the step of reacting an acetylenic (meth)acrylate of formula (III) or (IV)

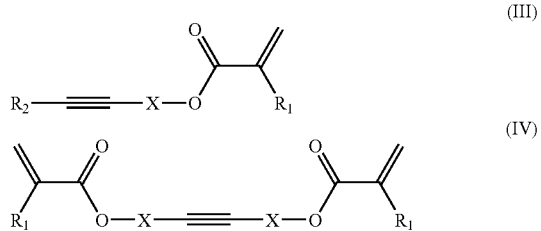

and an azide of formula (V)

Method (b) comprises the steps of reacting an acetylenic alcohol of formulae (VI) or (VII)

and an azide of formula (V)

to form an alcohol compound represented by formulae (VIII) or (IX)

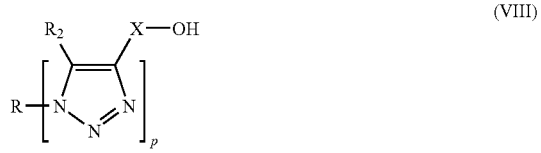

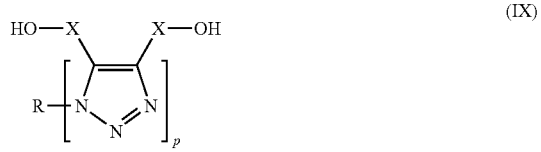

which (VIII) or (IX) is further reacted with a compound of formula (X),

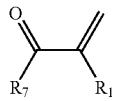

wherein $R_7$ is a halogen, OH or $OR_8$, $R_8$ is $C_{1-4}$ alkyl, and $R_1$, $R_2$, R and X and p are defined as in formula (I) or (II) above.

Polymers or copolymers formed from the new monomer family of formulae (I) and (II) may be used in such applications as pigment dispersants, polymeric electrolytes, fuel cell membranes, corrosion inhibitors, and personal care.

DETAILED DESCRIPTION OF THE INVENTION

Definitions

The term (meth)acrylic or (meth)acrylate encompasses acrylic, acrylate, methacrylic, and methacrylate.

The term monomer by itself refers to the monomer before polymerization.

Once the monomer is polymerized the monomer becomes a monomer unit.

The monomers of formulae (I) or (II) may be polymerized to form a polymer. The polymer may be a homopolymer or co-polymer.

The architecture of the formed polymer from the monomer(s) of formulae (I) or (II) may be of random, linear, crosslinked, structured, block, graft, or star architecture.

The polymer or co-polymer formed from formulae (I) or (II) may be polymerized by controlled polymerization methods.

The controlled polymerization methods are for example, atom transfer radical polymerization (ATRP or SET), nitroxide-mediated polymerization, reversible addition-fragmentation transfer polymerization (RAFT), and group-transfer polymerization.

In regard to the substituents of formulae (I) and (II):

$R_1$ $R_1$ is hydrogen or $C_{1-3}$ alkyl. $C_{1-3}$ alkyl for purposes of the invention means methyl, ethyl isopropyl or propyl.

$R_2$ $R_2$ is hydrogen, methyl, linear or branched $C_{2-30}$ alkyl, where said $C_{2-30}$ alkyl is optionally interrupted by O, S or Si, and is optionally further substituted by phenyl, $OR_3$, $COOR_4$ or $NR_5R_6$;

Linear or branched $C_{2-30}$ alkyl is for example $C_{2-22}$, $C_{2-18}$, $C_{2-12}$, $C_{2-8}$, $C_{2-6}$ or $C_{2-4}$ alkyl. Examples are: ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, stearyl, nonadecyl, eicosyl, henicosyl, docosyl, tricosyl, tetracosyl, pentacosyl, hexacosyl, octacosyl, nonacosyl, triacontyl, behenyl and mixtures thereof.

Linear or branched $C_{2-30}$ alkyl interrupted by oxygen, sulfur or silicon is for example $(CH_3)_3Si-$, $CH_3-O-CH_2-$, $CH_3-S-CH_2-$, $CH_3-O-CH_2-CH_2-O-CH_2-$, $CH_3-(O-CH_2-CH_2-)_2-O-CH_2-$, $CH_3-(O-CH_2-CH_2-)_3-O-CH_2-$, $CH_3-O-CH_2-CH_2-$, $-CH_2-CH(CH_3)-O-CH_2-$ or $CH_3-(O-CH_2-CH_2-)_4-O-CH_2-$ or $-[CH_2-CH(OH)]_y-CH_3$, wherein y=1-5.

$R_3$ and $R_4$ $R_3$ or $R_4$ is independently linear or branched $C_{1-10}$ alkyl or substituted or unsubstituted phenyl.

If $R_3$ or $R_4$ is phenyl, the phenyl may be unsubstituted or substituted as for example with $C_{1-4}$ alkyl or $C_{1-6}$ alkoxy.

Linear or branched $C_{1-10}$ alkyl is for example methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl or decyl.

$R_5$ and $R_6$ $R_5$ and $R_6$ are independently hydrogen, linear or branched $C_{1-10}$ alkyl, or $R_5$ and $R_6$ together may form a ring.

$R_5$ and $R_6$ may form a five- or six-membered heterocyclic ring. The heterocycle may for example be saturated or unsaturated, and may be further substituted. Heterocycles such as pyridine, piperidine, pyrrole, thiophene, imidazole and morpholine are envisioned.

The term heterocycle includes virtually any heterocyclic ring or rings.

X

X is methylene or linear or branched $C_{2-30}$ alkylene, optionally substituted by one or more phenyl, wherein $C_{2-30}$ alkylene is optionally interrupted by O or S;

Linear or branched $C_{2-30}$ alkylene is for example at least divalent. Suitable examples are $C_{2-8}$, $C_{2-6}$ or $C_{2-4}$ alkylene. Specific examples are ethylene, propylene, butylene, pentylene, hexylene, heptylene, octylene, nonylene, decylene, undecylene, dodecylene, tetradecylene, pentadecylene, hexadecylene, heptadecylene, octadecylene, nonadecylene, and eicosylene.

Methylene or linear or branched $C_{2-30}$ alkylene optionally substituted by one or more phenyl may be for example —CH(Ph)—, —C(Ph)$_2$- or —CH$_2$—CH(Ph)-.

The linear or branched $C_{2-20}$ alkylene optionally interrupted by oxygen or sulfur may be for example, —CH$_2$—O—CH$_2$—O—CH$_2$—, —CH$_2$—CH$_2$—O—CH$_2$—CH$_2$—, —CH$_2$—CH(CH$_3$)—O—CH$_2$—CH$_2$—CH$_2$—CH$_2$—S—CH$_2$—CH$_2$—CH$_2$— and —[CH$_2$—CH(OH)]$_y$—CH$_2$—, wherein y=1-5.

When p is 1:

R is hydrogen, methyl, linear or branched $C_{2-30}$ alkyl, cycloalkyl, $C_{2-30}$ alkenyl, aryl, aralkyl, heterocycloalkyl or heterocycloaryl, wherein the alkyl or alkenyl is optionally interrupted by O or S, and is optionally further substituted by one or more halogen, OH, $C_{1-4}$ haloalkyl, $C_{1-16}$ alkyl, phenyl, OR$_3$, COOR$_4$ or NR$_5$R$_6$;

Linear or branched $C_{2-30}$ alkyl is as defined above under $R_2$.

Cycloalkyl may be $C_{5-12}$ cycloalkyl and is for example substituted or unsubstituted aliphatic rings such as cyclopentyl, cyclohexyl, cycloheptyl or cyclooctyl.

Linear or branched $C_{2-30}$ alkenyl is for example $C_{2-30}$ carbon chains of varying unsaturation. For example $C_{2-30}$ alkenyl may be $C_{2-22}$, $C_{2-18}$ or $C_{2-12}$. The number of double bonds may be anywhere from 1 to 3. The double bonds may occur on internal sites of the chain or at the end. Some examples might be —CH$_2$—CH$_2$—CH$_2$—CH=CH$_2$, or —CH$_2$—CH$_2$—CH=CH—CH$_2$—CH$_2$—CH$_3$.

Aryl is for example any aromatic ring or rings. For example aryl may be substituted or unsubstituted phenyl, napthyl, carbazole, fluorene or biphenyl. Aryl may also include for example:

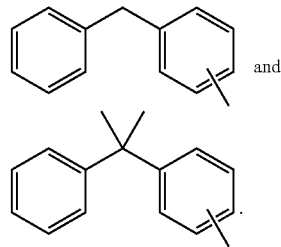
and

Suitable examples of aralkyl groups may contain 7-12 carbon atoms such as benzyl, 2-phenylethyl, α-methylbenzyl, α,α-dimethylbenzyl.

However, when p is 1, R excludes perfluorinated carbon chains. Furthermore, when p is 1, R is not 7-oxooxepanyl.

$C_{2-30}$ alkenyl interrupted by oxygen or sulphur is analogous to the $C_{2-30}$ alkyl examples above but in addition to interruption by oxygen or sulphur contain unsaturation.

Heterocycloalkyl embraces within the given structure one or two heterocyclic groups having one to four heteroatoms selected from the group consisting of nitrogen, sulfur and oxygen. Some examples of heterocycloalkyl are tetrahydrofurfuryl, pyrrolidinyl, piperazinyl, piperidinyl, and tetrahydrothienyl.

Some examples of heterocycloaryl are furyl, thiophenyl, imidazolyl, pyrrolyl, pyridyl and pyrimidinyl.

Optional substitution of the aryl, aryl of the aralkyl group, the cycloalkyl, the heterocyclic or the heterocycloaryl may include one or more halogen, OH, $C_{1-4}$ haloalkyl, $C_{1-16}$ alkyl, substituted or unsubstituted phenyl, OR$_3$, COOR$_4$ or NR$_5$R$_6$.

Halogen includes Cl, Br, I and F.

$C_{1-4}$ haloalkyl may be mono- or poly-substituted by halogen. Examples are chloromethyl, trichloromethyl, trifluoromethyl or 2-bromopropyl.

$C_{1-16}$ alkyl is linear or branched. Examples are methyl, ethyl, propyl, isopropyl, n-butyl, sec-butyl, isobutyl, tertbutyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl or stearyl.

When p is 2, 3 or 4,

R is a di-, tri- or tetra-valent linking group, said divalent linking group is a polymer, methylene, linear or branched $C_{2-20}$ alkylene, linear or branched $C_{2-30}$ alkenylene, cycloalkylene, arylene, aralkylene, heterocycloalkylene or heteroarylene, the $C_{2-30}$ alkylene or $C_{2-30}$ alkenylene is optionally interrupted by O or S and the aryl of the arylene group, the aryl of the aralkylene, the cycloalkylene, the heterocycloalkylene or the heteroarylene is optionally further substituted by one or more halogen, OH, $C_{1-4}$ haloalkyl, $C_{1-16}$ alkyl, phenyl, OR$_3$, COOR$_4$ or NR$_5$R$_6$;

The divalent linking group may be a polymer or co-polymer. For example, if R is a polymer, say a linear polyethylene oxide, the 1,2,3-triazole (meth)acrylate will at a minimum terminate each end of the polymer. The end-capped polymer may be formed for example by reacting the two terminal bromines of the polyethyleneglycol with an azide ion and then reacting the formed diazide with an acetylenic (meth) acrylate.

Cycloalkylene is for example $C_{5-12}$ cycloalkylene and is substituted or unsubstituted aliphatic rings such as cyclopentylene, cyclohexylene, cycloheptylene or cyclooctylene.

$C_{2-30}$ alkenylene is defined similarly as above for alkylene but contains unsaturation.

The number of double bonds may be anywhere from 1 to 3. The double bonds may occur on internal sites of the chain. Some examples are:

—$CH_2$—$CH_2$—$CH_2$—CH=$CH_2$—$CH_2$—, or —$CH_2$—$CH_2$—CH=CH—$CH_2$=$CH_2$—$CH_2$—.

Arylene is at least divalent and is for example, any aromatic ring or rings. For example arylene may be substituted or unsubstituted phenylene, naphthylene, biphenylene or oxy-diphenylene. Arylene may also include for example

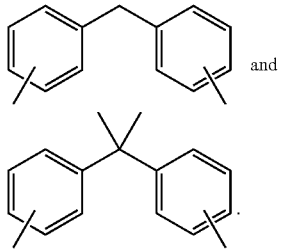

Phenylene or naphthylene each unsubstituted or substituted by $C_1$-$C_4$ alkyl is, for example, 1,2-, 1,3- or 1,4-phenylene, or 1,2-, 1,3-, 1,4-, 1,6-, 1,7-, 2,6- or 2,7-naphthylene.

Aralkylene is for example a phenylalkylene and may encompass $C_{7-20}$ phenylalkylidene or $C_7$-$C_9$ phenylalkylidene. Specific examples are benzylidene, 2-phenylethylidene or 1-phenyl-2-hexylidene.

Heterocycloalkylene or heterocycloarylene groups are analogous to heterocycloalkyl or heterocycloaryl above except that the groups form a di-, tri- or tetra-valent bridging group.

Heterocycloalkylene embraces within the given structure one or two heterocyclic groups having one to four heteroatoms selected from the group consisting of nitrogen, sulfur and oxygen. Some examples of heterocycloalkylene are tetrahydrofurylene, pyrrolidinylene, piperazinylene and tetrahydrothiophenylene.

Some examples of heterocycloarylene are furylene, thiophenylene, pyrrolylene, pyridylene and pyrimidinylene.

Linear or branched $C_{2-30}$ alkylene, optionally interrupted by O or S are defined as above under "X".

$C_{2-30}$ alkenylene interrupted by oxygen or sulphur is analogous to the $C_{2-30}$ alkyl examples above but in addition to interruption by oxygen or sulphur contain unsaturation.

Examples of Monomers of Formulae (I) or (II)

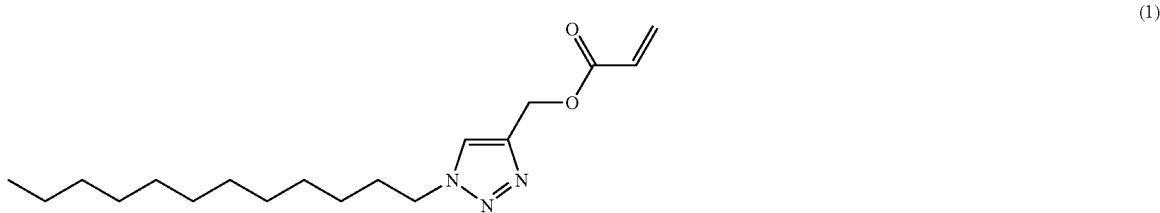

(1)

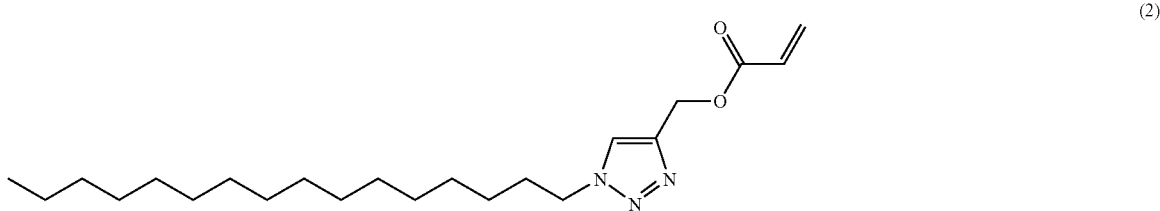

(2)

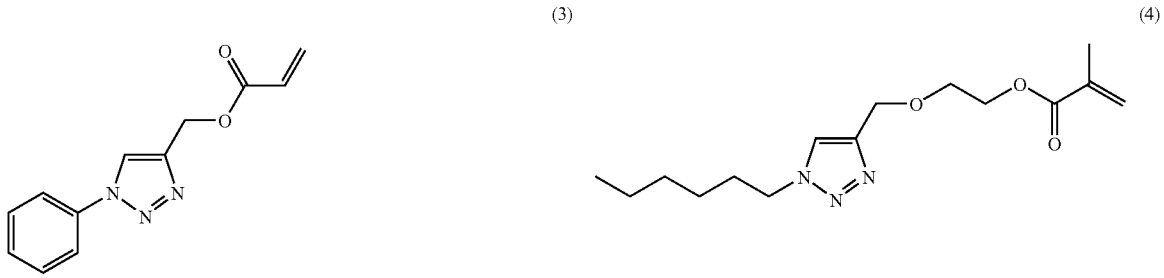

(3) (4)

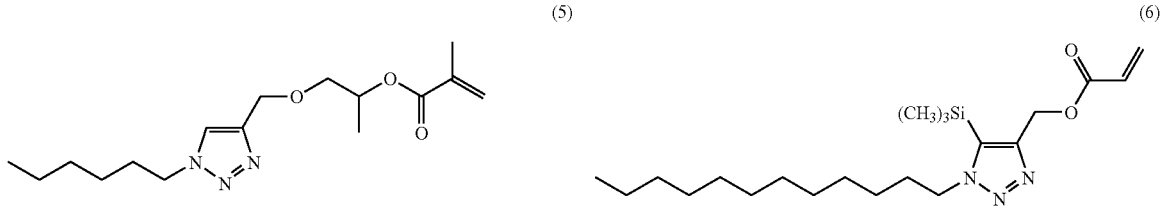

(5) (6)

-continued

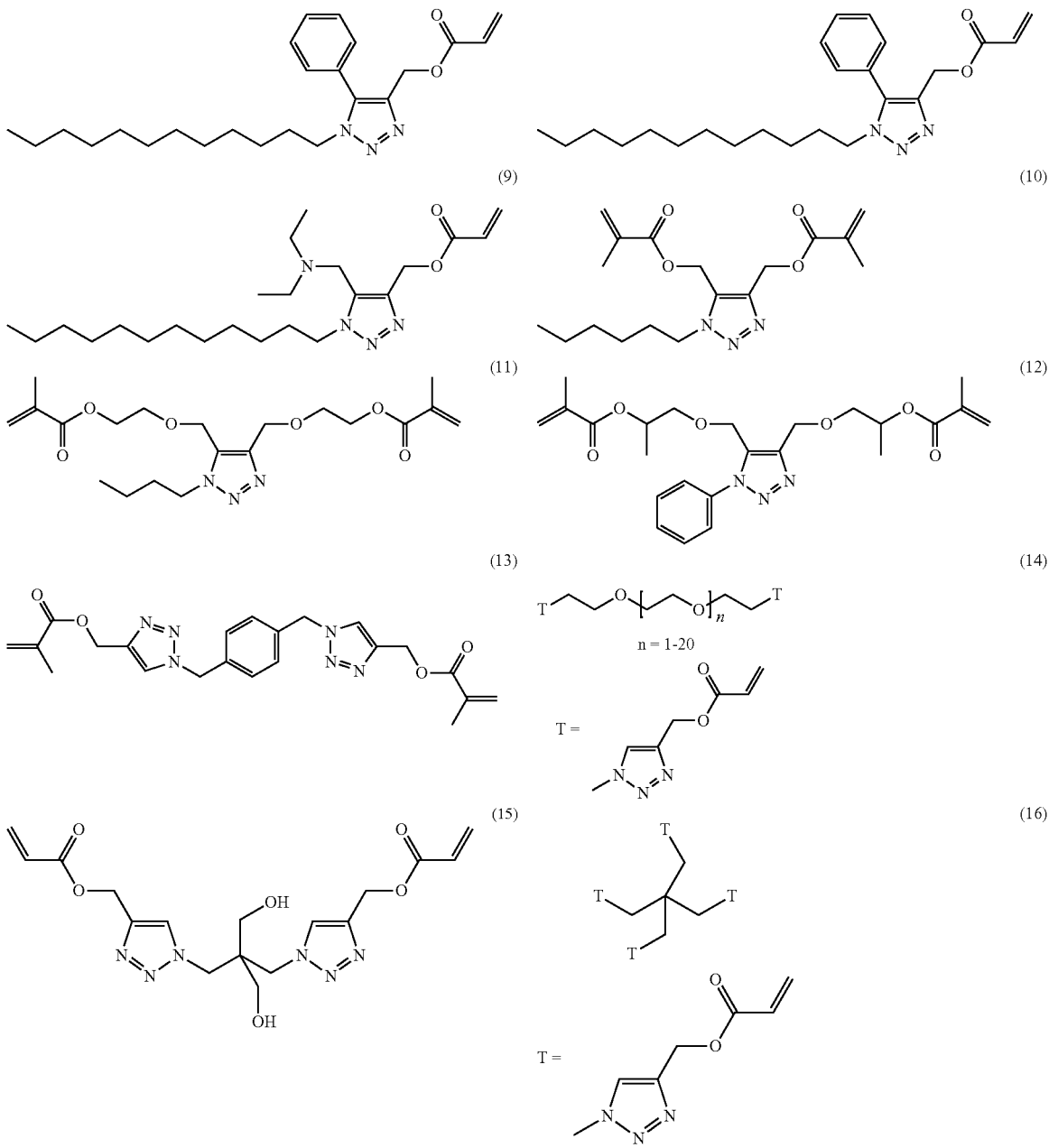

The above monomers may be formed by various methods. For example, an azido pendant R group as defined above may be directly reacted with an acetylenic (meth)acrylate such as propargyl(meth)acrylate using a copper catalyst. Alternatively, an azido pendant R group as defined above may be reacted with a acetylenic alcohol such as propargyl alcohol or 3-trimethylsilyl-2-propyn-1-ol which is further reacted with (meth)acryloyl chloride. Both methods are virtually quantitative.

The azido-functionalized R may be formed by well known methods in the art. For example, nucleophilic substitution of alkyl halides or tosylates by azide ion is a well-established general synthetic pathway to alkyl azides. The reaction can be done in organic solvents, alcohol-water mixtures, or under phase-transfer conditions. Lewis acid catalysis may be used with tertiary or activated alkyl halides and alcohols. Besides sodium azide, other reagents employed are tetraalkylammonium or guanidium azides, or polymeric quaternary ammonium azides. Cu(I)-catalysis promotes coupling of the less reactive aryl or vinyl halides with sodium azide, allowing production of aryl or vinyl azides at low temperature in good to excellent yields.

Several acetylenic alcohols are available commercially and can be esterified by methods well known in the art to give the corresponding acrylate or methacrylate esters. Propargyl acrylate, propargyl methacrylate and 3-trimethylsilyl-2-propyn-1-ol are available from companies like Aldrich, ABCR, Alfa Aesar, PolySciences, and Monomer-Polymer and Dajac Laboratories.

The reaction between the acetylenic functionality and the azido groups is catalyzed by Cu(I). The copper catalyst may be copper tunings, copper salts or Cu(I) complexes. For example, copper salts may be copper halides such as CuI and CuBr.

Tetrakis(acetonitrile) Cu(I) hexafluorophosphate is an excellent copper catalyst for this reaction. The catalyst may further include a chelating agent to increase its solubility. Such chelating agent may be N,N,N',N'',N''-pentamethyldiethylenetriamine.

The solvents for reacting the acetylenic groups with azido groups depend on the solubility of the intermediates.

The polymers formed from the monomers of formula (I) or (II) are prepared by polymerizing the novel monomers under typical polymerization conditions.

The polymers formed from the monomer of formula (I) or (II) may be used for such various applications as pigment dispersants, polymeric electrolytes, fuel cell membranes, corrosion inhibitors, and personal care. The polymers formed from monomer of formula (I) or (II) may also be incorporated into coating formulations which in turn may provide improved corrosion protection and adhesion of the coating to metals.

EXAMPLES

Example 1

1-Dodecyl-4-acryloyloxymethyl-triazole

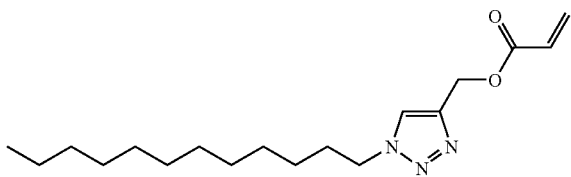

Propargyl acrylate (13 g, 0.118 mmoles), dodecyl azide (22.3 g, 0.118 mmoles) and tetrakis(acetonitrile)copper (I) hexafluorophosphate (0.75 g, 2 mmoles) are dissolved in DMF (200 ml) and stirred at room temperature under nitrogen for 24 hours. The reaction mixture is poured into water wherefrom the product precipitated as a white crystalline solid (33.5 g; yield 95%; mp 50-52° C.). $^1$H NMR (CDCl$_3$, δ ppm) 7.78 (broad, 1H), 6.42 (d, 1H), 6.16 (dd, 1H), 5.82 (d, 1H), 5.30 (s, 2H), 4.32 (t, 2H), 1.92 (t, 2H), 1.28 (m, 20H), 0.88 (t, 3H). $^{13}$C NMR (CDCl$_3$, δ ppm) 165.7, 142.4, 131.1, 127.9, 123.5, 57.6, 57.5, 50.2, 31.7, 30.1, 29.4, 29.3, 29.2, 29.1, 28.8, 26.3, 22.4, 13.9.

Example 2

1-Hexadecyl-4-acryloyloxymethyl-triazole

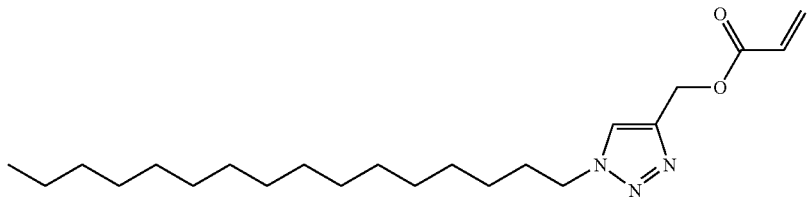

Propargyl acrylate (1.10 g, 10 mmoles), hexadecyl azide (2.37 g, 10 mmoles) and tetrakis(acetonitrile)copper (I) hexafluorophosphate (74 mg, 0.2 mmoles) are dissolved in DMF (20 ml) and stirred at room temperature under nitrogen for 24 hours. The reaction mixture is poured into water wherefrom the product precipitated as a white crystalline solid (2.95 g; yield 85%; mp 72-73° C.). $^1$H NMR (CDCl$_3$, δ ppm) 7.61 (s, 1H), 6.44 (d, 1H), 6.14 (dd, 1H), 5.85 (d, 1H), 5.31 (s, 2H), 4.34 (t, 2H), 1.92 (q, 2H), 1.26 (m, 28H), 0.88 (t, 3H). $^{13}$C NMR (CDCl$_3$, δ ppm) 166.00, 142.73, 131.39, 128.04, 123.64, 57.75, 50.43, 31.89, 30.22, 29.66, 29.65, 29.64, 29.62, 29.61, 29.56, 29.47, 29.33, 29.32, 28.95, 26.46, 22.66, 14.08. MS for $C_{12}H_{39}N_3O_2$ calculated 377.58; found 377.20.

Example 3

1-Phenyl-4-acryloyloxymethyl-triazole

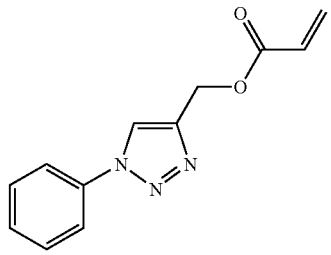

Propargyl acrylate (13.5 g, moles), phenyl azide (12.5 g, moles) and tetrakis(acetonitrile)copper (I) hexafluorophosphate (0.84 g, 2.3 mmoles) are dissolved in DMF (100 ml) and stirred at room temperature under nitrogen for 24 hours. The reaction mixture is poured in water and the product is extracted with ethyl acetate. The solvent is distilled under reduced pressure, and mixed with diethyl ether wherefrom the product crystallized as an off-white, crystalline solid (23 g; yield 89%; mp 55-56° C.). $^1$H NMR (CDCl$_3$, δ ppm) 8.08 (s, 1H), 7.72 (d, 2H), 7.51 (t, 2H), 7.44 (q, qH), 6.48 (d, 1H), 6.17 (q, 1H), 5.88 (d, 1H), 5.50 (s, 2H). $^{13}$C NMR (CDCl$_3$, δ ppm) 165.9, 143.4, 136.8, 131.5, 129.7, 128.8, 127.8, 122.1, 120.5, 57.5.

I claim:
1. Monomers represented by formulae (I) or (II):

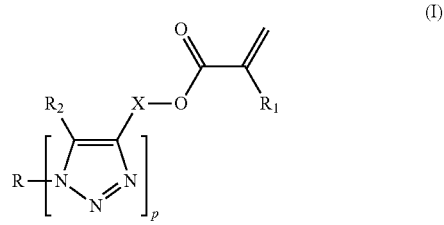
(I)

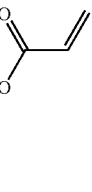

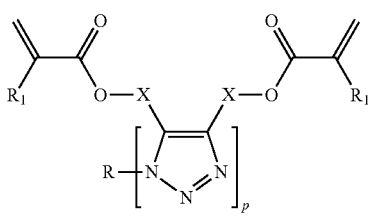

(II)

wherein
$R_1$ is hydrogen or $C_{1-3}$ alkyl,
$R_2$ is hydrogen, methyl, linear or branched $C_{2-30}$ alkyl,
  where said $C_{2-30}$ alkyl is optionally interrupted by O, S or Si,
  and is optionally further substituted by phenyl, $OR_3$, $COOR_4$ or $NR_5R_6$;
X is methylene or linear or branched $C_{2-30}$ alkylene, optionally substituted by one or more phenyl,
  wherein $C_{2-30}$ alkylene is optionally interrupted by O or S;
p is 1, 2, 3 or 4;
when p is 1,
R is hydrogen, methyl, linear or branched $C_{2-30}$ alkyl, cycloalkyl, $C_{2-30}$ alkenyl, aryl, aralkyl, heterocycloalkyl or heterocycloaryl,
  wherein the alkyl or alkenyl is optionally interrupted by O or S,
  and
  is optionally further substituted by one or more, OH, $C_{1-16}$ alkyl, phenyl, $OR_3$, $COOR_4$ or $NR_5R_6$;
when p is 2, 3 or 4,
R is a di-, tri- or tetra-valent linking group,
  said linking group is a polymer, methylene, linear or branched $C_{2-20}$ alkylene, cycloalkylene, linear or branched $C_{2-30}$ alkenylene, arylene, aralkylene, heterocycloalkylene or heterocycloarylene,
  the $C_{2-30}$ alkylene or $C_{2-30}$ alkenylene is optionally interrupted by O or S,
  and
  the aryl or the arylene group, the aryl of the aralkyl, the cycloalkylene, the heterocycloalkylene or heterocycloarylene is optionally further substituted by one or more halogen, OH, $C_{1-4}$ haloalkyl, $C_{1-16}$ alkyl, substituted or unsubstituted phenyl, $OR_3$, $COOR_4$ or $NR_5R_6$;
$R_3$ is linear or branched $C_{1-10}$ alkyl or phenyl;
$R_4$ is linear or branched $C_{1-10}$ alkyl or phenyl;
and
$R_5$ and $R_6$ are independently hydrogen, linear or branched $C_{1-10}$ alkyl, or $R_5$ and $R_6$ together form a ring.

2. Monomer of formula (I) according to claim 1, wherein X is linear or branched $C_{2-6}$ alkylene, optionally interrupted by O.

3. Monomers according to claim 1, wherein
p is 2, 3 or 4 and
R is a polymer or linear or branched $C_{2-30}$ alkylene.

4. A polymer or co-polymer formed from the monomers described by formulae (I) or (II) according to claim 1.

5. The polymer or co-polymer according to claim 4, wherein the polymer is at least partially formed by a controlled polymerization method.

6. The polymer or co-polymer according to claim 5, wherein the controlled polymerization method is atom transfer radical polymerization (ATRP), nitroxide-mediated polymerization, reversible addition-fragmentation transfer polymerization (RAFT), or group transfer polymerization.

7. A method of preparing the monomers of formula (I) or (II) according to claim 1 by either method (a) or method (b), wherein method (a) comprises the step of
reacting an acetylenic (meth)acrylate represented by formula (III) or (IV)

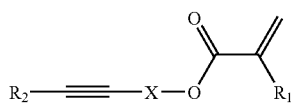

(III)

(IV)

and an azide of formula (V)

(V)

And method (b) comprises the steps of
reacting an acetylenic alcohol of formulae (VI) or (VII)

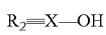

(VI)

(VII)

and
an azide of formula (V)

(V)

to form an alcohol compound represented by formulae (VIII) or (IX)

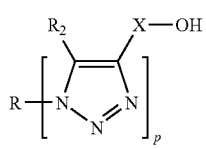

(VIII)

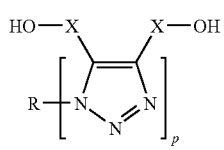

(IX)

which (VIII) or (IX) is further reacted with a compound of formula (X),

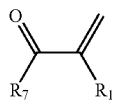

(X)

wherein $R_7$ is a halogen, OH or $OR_8$,
$R_8$ is $C_{1-4}$ alkyl,
and
$R_1$, $R_2$, R and X and p are defined as in formula (I) and (II) according to claim 1.

8. The method according to claim 7, wherein the compound of formula (III) is propargyl acrylate or propargyl methacrylate.

9. The method according to claim 7, wherein the compound of formula (VI) is propargyl alcohol or 3-trimethylsilyl-2-propyn-1-ol.

10. A coating, pigment dispersant, polymeric electrolyte, anticorrosion agent or personal care product comprising the polymer according to claim 4.

11. Monomers represented by formulae (I) or (II):

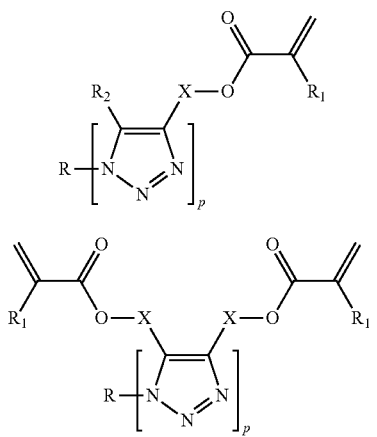

wherein
$R_1$ is hydrogen or $C_{1-3}$ alkyl,
$R_2$ is hydrogen, methyl, linear or branched $C_{2-30}$ alkyl,
where said $C_{2-30}$ alkyl is optionally interrupted by O, S or Si,
and is optionally further substituted by phenyl, $OR_3$, $COOR_4$ or $NR_5R_6$;
X is methylene or linear or branched $C_{2-30}$ alkylene, optionally substituted by one or more phenyl,
wherein $C_{2-30}$ alkylene is optionally interrupted by O or S;
p is 2, 3 or 4;
when p is 2, 3 or 4,
R is a di-, tri- or tetra-valent linking group,
said linking group is a polymer, methylene, linear or branched $C_{2-20}$ alkylene, cycloalkylene, linear or branched $C_{2-30}$ alkenylene, arylene, aralkylene, heterocycloalkylene or heterocycloarylene,
the $C_{2-30}$ alkylene or $C_{2-30}$ alkenylene is optionally interrupted by O or S,
and
the aryl or the arylene group, the aryl of the aralkyl, the cycloalkylene, the heterocycloalkylene or heterocycloarylene is optionally further substituted by halogen, OH, $C_{1-16}$ alkyl, $C_{1-4}$ haloalkyl, substituted or unsubstituted phenyl, $OR_3$, $COOR_4$ or $NR_5R_6$;
$R_3$ is linear or branched $C_{1-10}$ alkyl or phenyl;
$R_4$ is linear or branched $C_{1-10}$ alkyl or phenyl;
and
$R_5$ and $R_6$ are independently hydrogen, linear or branched $C_{1-10}$ alkyl, or $R_5$ and $R_6$ together form a ring.

* * * * *